(12) United States Patent
Tsuji et al.

(10) Patent No.: US 7,153,573 B2
(45) Date of Patent: Dec. 26, 2006

(54) POLYMER COMPOSITE PARTICLE COMPRISING METAL OXIDE AND SILICONE AND/OR FLUORINE AND METHOD OF PRODUCING THE SAME

(75) Inventors: Makoto Tsuji, Wakayama (JP); Hiromi Nambu, Wakayama (JP); Makoto Inoue, Wakayama (JP); Satoshi Sugawara, Tokyo (JP); Yukio Inomata, Tokyo (JP)

(73) Assignee: Kao Corporation, Tokyo (JP)

( * ) Notice: Subject to any disclaimer, the term of this patent is extended or adjusted under 35 U.S.C. 154(b) by 487 days.

(21) Appl. No.: 10/630,741

(22) Filed: Jul. 31, 2003

(65) Prior Publication Data

US 2004/0071956 A1  Apr. 15, 2004

(30) Foreign Application Priority Data

| Aug. 8, 2002 | (JP) | ............................. 2002-231271 |
| Feb. 28, 2003 | (JP) | ............................. 2003-052325 |
| Mar. 12, 2003 | (JP) | ............................. 2003-067288 |

(51) Int. Cl.
*B32B 5/16* (2006.01)

(52) U.S. Cl. ...................... 428/403; 428/407; 524/730; 524/779; 524/795

(58) Field of Classification Search ................ 428/403, 428/407; 524/457, 779, 780, 783, 795, 730
See application file for complete search history.

(56) References Cited

U.S. PATENT DOCUMENTS

| 3,716,505 A * | 2/1973 | Ohe et al. .................... 524/733 |
| 4,801,445 A * | 1/1989 | Fukui et al. .................. 424/69 |
| 6,132,861 A | 10/2000 | Kang et al. |
| 6,224,852 B1 * | 5/2001 | Morgan et al. ............... 424/59 |
| 6,451,941 B1 * | 9/2002 | Urashima et al. ........... 526/212 |
| 6,475,500 B1 * | 11/2002 | Vatter et al. ................ 424/401 |

(Continued)

FOREIGN PATENT DOCUMENTS

EP  0 317 272  5/1989

(Continued)

OTHER PUBLICATIONS

Patent Abstracts of Japan, JP 02-187402, Jul. 23, 1990 (corr. US 5,420,177).

(Continued)

*Primary Examiner*—H. Thi Le
(74) *Attorney, Agent, or Firm*—Oblon, Spivak, McClelland, Maier & Neustadt, P.C.

(57) ABSTRACT

The invention provides a polymer composite particle having superb blending stability even in a W/O emulsion cosmetic, a highly effective ultraviolet protection effect and a good feeling in use. The invention also relates to a method of producing the polymer composite particle and a cosmetic composition containing the polymer composite particle. A preferred polymer composite particle contains a metal oxide coated with a silicone and/or fluorine compound and has an average particle diameter of 1 μm or less, wherein the polymer composite particle is obtained by polymerizing a crosslinking agent with a vinyl monomer contained in an amount of 25% by weight based on 100% by weight of the sum of total of all the monomers and crosslinking agent and wherein the vinyl monomer has a solubility parameter calculated by the Fedors method of less than about 8.9. A preferred cosmetic composition may contain (A) a microparticle metal oxide having an average primary particle diameter of from 0.001 to 0.1 μm, and (B) a flake zinc oxide having an average primary particle size of from 0.1 μm to 1 μm and an average thickness of from 0.01 μm to 0.2 μm, which provides ultraviolet protection ability and visible-light transmittance.

14 Claims, 2 Drawing Sheets

1.5 μm

U.S. PATENT DOCUMENTS

| | | | |
|---|---|---|---|
| 6,524,705 B1 * | 2/2003 | O'Lenick et al. | 428/402 |
| 6,599,631 B1 * | 7/2003 | Kambe et al. | 428/447 |
| 6,610,278 B1 * | 8/2003 | Kashimoto | 424/64 |
| 2002/0094439 A1 | 7/2002 | Edelmann et al. | |
| 2002/0197475 A1 | 12/2002 | Edelmann et al. | |

FOREIGN PATENT DOCUMENTS

| | | |
|---|---|---|
| EP | 0 659 786 | 6/1995 |
| EP | 0 887 067 | 12/1998 |
| JP | 4-132702 | 5/1992 |
| JP | 9-208437 | 8/1997 |
| JP | 9-235217 | 9/1997 |
| WO | WO 99/57205 | 11/1999 |
| WO | WO 99/57375 | 11/1999 |
| WO | WO 00/05284 | 2/2000 |
| WO | WO 01/18082 | 3/2001 |
| WO | WO 01/81466 | 11/2001 |
| WO | WO 03/060014 | 7/2003 |

OTHER PUBLICATIONS

Patent Abstracts of Japan, JP 57-120514, Jul. 27, 1982.
Patent Abstracts of Japan, JP 09-208437, Aug. 12, 1997.
Patent Abstracts of Japan, JP 2002-121421, Apr. 23, 2002.

* cited by examiner 1.5 μm

500nm 1.5 μm

500nm 1.5 μm

500nm

POLYMER COMPOSITE PARTICLE COMPRISING METAL OXIDE AND SILICONE AND/OR FLUORINE AND METHOD OF PRODUCING THE SAME

TECHNICAL FIELD

The present invention relates to a polymer composite particle containing a metal oxide, a method of producing a polymer composite particle and a cosmetic comprising the polymer composite particle.

BACKGROUND OF THE INVENTION

Ultraviolet absorbers are formulated in cosmetics for the purpose of protecting bare skin from ultraviolet rays. These ultraviolet absorbers may be roughly classified into organic types and inorganic types. Examples of the former include cinnamic acid derivatives, benzophenone derivatives, methylaminobenzoic acid derivatives and salicylic acid derivatives. Examples of the latter include metal oxides such as zinc oxide, titanium oxide, cerium oxide and iron oxide. In the case of organic ultraviolet absorbers, there is the problem that these absorbers have a low absorption wavelength region, are constituted of unstable compounds and penetrate into the skin so that the effect of these absorbers does not last long. In the case of inorganic ultraviolet absorbers, there is the problem that these absorbers have less dispersibility in a product formulation and not much good feeling in use.

Capsulation of metal oxides is known as one proposal for making compatible dispersibility in a product formulation and a good feeling in use. For example, in JP-A 9-208437, a cosmetic is disclosed which is prepared by coating a metal oxide having an average particle diameter of 0.003 to 0.1 μm with a resin powder, in an emulsion cosmetic. However, because an ionic dispersant is used to disperse the metal oxide in this method, the hydrophilic portions of the metal oxide aggregate in the W/O emulsion cosmetic in the case where the metal oxide partly exists on the surface of the resin powder, and therefore the stability of the formulation is impaired and protection from ultraviolet rays is ineffective.

Also, in another attempt, studies have been made concerning cosmetics combining protection from ultraviolet rays and a good feeling in use by using a combination of several powders. For example, in JP-A 9-235217, cosmetics containing inorganic powders are disclosed in which silica having a particle diameter of 0.01 to 10 μm is coated with zinc oxide, and in which a super-microparticle titanium oxide having a particle diameter of 0.001 to 0.10 μm is coated with a plate talc, mica and/or sericite.

However, when the resin powder in which these metal oxides are coated is used alone or in combination with a super-microparticle titanium oxide, a cosmetic having an effective UVA protection and a good feeling in use cannot be obtained.

SUMMARY OF THE INVENTION

The present invention relates to a polymer composite particle having a metal oxide coated with a silicone and/or fluorine compound, the metal oxide having an average particle diameter of 1 μm or less. The polymer composite particle is obtained by polymerizing a vinyl monomer with a crosslinking agent, wherein the vinyl monomer is contained in an amount of 25% or more weight based on 100% weight of the sum of the whole monomer and crosslinking agent. The vinyl monomer has a solubility parameter (calculated by the Fedors method) of less than about 8.9. The vinyl monomer has a solubility parameter, preferably, of less than 8.9.

The present invention also relates to a polymer composite particle comprising a metal oxide coated with a silicone and/or fluorine compound, the metal oxide having an average particle diameter of 1 μm or less, wherein a cosmetic comprising the polymer composite particle in an amount corresponding to 5% by weight of the metal oxide and 1% by weight of 2-ethylhexyl 4-methoxycinnamate has an SPF of 7 or more.

The present invention also relates to a method of producing the polymer composite particle, a cosmetic comprising the cosmetic polymer composite particle, and a cosmetic use of the polymer composite particle.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which:

DETAILED DESCRIPTION OF THE INVENTION

Figure 1:
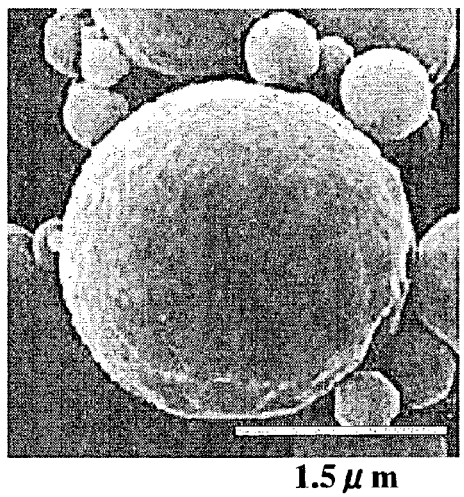
FIG. 1 is a scanning type electron microphotograph of a polymer composite particle obtained in Example 1.

All publications cited herein are hereby incorporated by reference.

The term "W/O" as used herein means water-in-oil.

The present invention relates to a polymer composite particle having superb blending stability even in a W/O emulsion cosmetic, highly effective ultraviolet protection and a good feeling in use; the present invention also relates to a method of producing the polymer composite particle and a cosmetic composition comprising the polymer composite particle.

The present invention also relates to a highly effective ultraviolet protection cosmetic, particularly highly effective in protection from ultraviolet rays having long wavelengths, having visible-light transmittance (as defined below)) and a good feeling in use.

The inventors of the present invention have found that the use of a combination of three type of powders including a microparticle metal oxide having the effect of protecting from ultraviolet rays ranging widely from UVB to UVAII and visible light transmittance, a zinc oxide having a flake particle shape and being highly effective in scattering light ranging from UVAII to UVAI close to visible light, and a polymer composite particle containing a coated microparticle metal oxide makes it possible to improve ultraviolet protection efficiently and to obtain an ultraviolet protection cosmetic having visible-light transmittance when applied and a good feeling in use.

[Polymer Composite Particle]

The polymer composite particle of the present invention has an average particle diameter of preferably from 0.1 to 20 μm and more preferably from 1 to 20 μm from the viewpoint of highly effective ultraviolet protection and an excellent feeling in use. When the particle diameter is too small, a frictional feeling is caused and therefore the particle diameter is preferably 0.1 μm or more. The shape of the particle is preferably spherical in view of an excellent feeling in use though no particular limitation is imposed on it.

The average particle diameter of the polymer composite particle is a volume average particle diameter measured using a laser (light) diffraction/scattering method (LA-910, manufactured by Horiba, Ltd.) or an electric resistance method (Coulter counter).

The content of the metal oxide in the polymer composite particle of the present invention is preferably from 25 to 90% by weight and more preferably from 30 to 70% by mass based on the whole polymer composite particle. In this range, the polymer composite particle has a highly effective ultraviolet protectionability.

The polymer composite particle of the present invention preferably has an SPF of 7 or more, in which SPF is measured using the same method as in the case of measuring SPF in the formulation of Test Example 1 which will be explained later.

Namely, the polymer composite particle of the present invention is a polymer composite particle comprising a metal oxide coated with a silicone and/or fluorine compound, wherein the metal oxide has an average particle diameter of 1 μm or less. The cosmetic comprising the polymer composite particle in an amount corresponding to 5% by weight of the metal oxide and 1% by weight of 2-ethylhexyl 4-methoxycinnamate has an SPF of 7 or more.

In order for a cosmetic comprising the polymer composite particle in an amount corresponding to 5% by weight of the metal oxide and 1% by weight of 2-ethylhexyl 4-methoxycinnamate to have an SPF of 7 or more in the measuring method which will be explained later, the metal oxide must be sufficiently dispersed in the cosmetic. Therefore, the SPF is a dispersion index showing that the metal oxide is properly dispersed in the polymer composite particle.

[Metal Oxide]

Examples of the metal oxide include silicon dioxide, iron oxide, zirconium oxide, aluminum oxide, zinc oxide, titanium oxide and cerium oxide. One or more types selected from the group consisting of zinc oxide, titanium oxide and/or cerium oxide, including mixtures, are preferable.

As the metal oxide, a metal oxide coated with a silicone and/or fluorine compound is used. Making the metal oxide hydrophobic by coating with a silicone and/or fluorine compound improves dispersibility in a monomer. Also, even if the metal oxide is present on the surface of the polymer composite particle, aggregation among polymers is prevented and also highly effective ultraviolet protection is obtained since the surface of the metal oxide is made hydrophobic.

The surface treatment of the metal oxide is preferably carried out to coat the metal oxide with a silicone and/or fluorine compound with a treating agent. Examples of the treating agent include methyl hydrogen polysiloxane, dimethylpolysiloxane, reactive alkylpolysiloxanes having a hydroxy group, halogen atom, amino hydrogen group or alkoxy group (these functional groups may be present at one terminal, both terminals or the side chain or may be connected to the silicon atom either directly or through a divalent hydrocarbon group which may have a substituent) as described in the publication of JP-A No. 5-339518 and the publication of JP-A No. 7-196946 and fluorine-containing hydrogen polysiloxanes as described in the publication of JP-A No. 6-23262. These agents may be reacted with the metal oxide by heating or the like. Also, commercially available metal oxides coated with a silicone and/or fluorine compound may be used.

The amount of the silicone and/or fluorine compound to be applied is preferably 0.1 to 20% by weight and more preferably 1 to 10% by weight based on 100% by weight of the metal oxide.

The average particle diameter of the metal oxide is preferably 1 μm or less, more preferably 0.01 to 1 μm and even more preferably 0.1 to 1 μm from the viewpoint of improving the effectiveness of ultraviolet protection and the visible-light transmittance of the polymer composite particle.

The average particle diameter of the metal oxide is a volume average particle diameter measured by a dynamic light scattering method (ELS-8000 manufactured by Otsuka Electronics Co., Ltd.)

[Monomer]

As the vinyl monomer to be used as a raw material of the polymer composite particle of the present invention, a monomer having a solubility parameter preferably less than about 8.9, more preferably about 8.8 or less, is used from the viewpoint of increased dispersibility and reduced uniformity of the metal oxide in the particle. The lower limit of the solubility parameter is preferably 6.0 or more and more preferably 7.0 or more in view of the availability of the monomer. The solubility parameter is a value obtained by rounding numbers off to the first decimal place. When the solubility parameter is high, the metal oxide is uniformly dispersed in the monomer. However, in the polymer composite particle after being polymerized, the metal oxide are gathered in the vicinity of the surface layer, bringing about a decrease in the effectiveness of protection from ultraviolet rays.

The solubility parameter used in this specification is a value $\delta$ $(cal/cm^3)^{1/2}$ (hereinafter also referred to an SP value) calculated from the following equation (I) according to the Fedors method [R. F. Fedors. Polyme. Eng. Sic., 14, 147 (1974)]

$$SP = \left(\frac{\sum \Delta ei}{\sum \Delta vi}\right)^{1/2}$$

Examples of the vinyl monomer having a solubility parameter less than about 8.9 include alkyl (meth)acrylates having a straight-chain or branched alkyl group which may be fluorinated and has 8 or more carbon atoms (preferably 8 to 40 carbon atoms) and more preferably alkyl (meth)acrylates having a straight-chain or branched alkyl group which may be fluorinated and has 10 to 22 more carbon atoms and dimethylpolysiloxane compounds having a radical polymerizable group at one terminal of a molecular chain. Here, the (meth)acrylate means an acrylate or a methacrylate. Specific examples of the (meth)acrylate include octyl(meth)acrylate, 2-ethylhexyl(meth)acrylate, lauryl(meth)acrylate, myristyl(meth)acrylate, palmityl (meth)acrylate, stearyl(meth)acrylate, isostearyl(meth)acrylate, behenyl(meth)acrylate and 2-(perfluoroalkyl)ethyl (meth)acrylates having 6 or more carbon atoms. The dimethylpolysiloxane compound having a radical polymerizable group at one terminal is preferably a compound represented by the formula (II) as described below and in the publication of JP-A No. 11-181003.

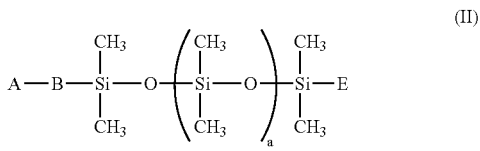

(II)

[In the Formula;

A: represents a group represented by $CH_2=C(R^1)COO-$, $CH_2=C(R^1)CONR^2-$ or $CH_2=CH-C_6H_4-$, where $R^1=H$ or $CH_3$, $R^2=H$ or $C_yH_{2y+1}$ (Y is an integer from 1 to 4);

B: represents a group represented by $-(CH_2O)_m-C_nH_{2n}-$ (m=0 or 1 and n=an integer from 1 to 10);

E: represents a group represented by $C_pH_{2p+1}$ (p=an integer from 1 to 4); and a: represents a number from 3 to 1500.

Although no particular limitation is imposed on the number average molecular weight (Mn) of the dimethylpolysiloxane compound having a radical polymerizable group at one terminal, dimethylpolysiloxane compounds having a number average molecular weight of from 500 to 100,000 are preferable and dimethylpolysiloxane compounds having a number average molecular weight of from 1,000 to 50,000 are more preferable.

Vinyl monomers, such as styrene and methylmethacrylate, having a solubility parameter of about 8.9 or more may be copolymerized as far as the effect of the present invention is not impaired. The amount of the vinyl monomer having a solubility parameter less than about 8.9 is preferably 25% by weight or more, more preferably 40% by weight or more, preferably 99.9% by weight or less, more preferably 97% by weight or less and even more preferably 90% by weight or less, based on 100% by weight of all the monomers and the crosslinking agent in total.

[Crosslinking Agent]

A crosslinking agent is used in the present invention to make firm the film of the polymer composite particle physically and chemically. Examples of crosslinking agents include crosslinkable vinyl compounds having at least two radical polymerizable groups (reactive unsaturated groups) in their molecules.

Specific examples of the crosslinkable vinyl compound having at least two radical polymerizable groups include (1) (meth)acrylate compounds of polyhydric alcohols having two or more (meth)acrylate residues such as ethylene glycol di(meth)acrylate, diethylene glycol di(meth)acrylate, triethylene glycol di(meth)acrylate, polyethylene glycol di(meth)acrylate, 1,3-butanedioldi(meth)acrylate, 1,4-butanedioldi(meth)acrylate, 1,6-hexanedioldi(meth)acrylate, neopentyl glycol di(meth)acrylate, 1,10-decanedioldi(meth)acrylate, propylene glycol di(meth)acrylate, polypropylene glycol di(meth)acrylate, trimethylolpropanetri(meth)acrylate, pentaerythritol tri(meth)acrylate, pentaerythritol tetra(meth) acrylate and dipentaerythritol hexa(meth)acrylate; (2) acrylamide compounds such as N-methylallylacrylamide, N-vinyladrylamide, N,N'-methylenebis(meth)acrylamide and bisacrylamidoacetic acid; (3) divinyl compounds such as divinylbenzene, divinyl ether and divinylethyleneurea; (4) polyallyl compounds such as diallyl phthalate, diallyl maleate, diallylamine, triallylamine, triallylammonium salts, allyl etherealized bodies of pentaerythritol and allyl etherealized bodies of sucrose having at least two allyl ether units in their molecules; and (5) (meth)acrylates of unsaturated alcohols such as vinyl(meth)acrylate, allyl(meth) acrylate and 2-hydroxy-3-acryloyloxypropyl(meth)acrylate.

The amount of the crosslinking agent is preferably 0.1% by weight or more, more preferably 3% by weight or more and even more preferably 10% by weight or more with the upper limit thereof being preferably 75% by weight or less, more preferably 60% by weight or less and even more preferably 55% by weight or less, based on 100% by weight of the sum of all monomers and the crosslinking agent.

[Method of Producing the Polymer Composite Particle]

The polymer composite particle of the present invention may be produced by the first step (hereinafter referred to as step 1) of dispersing/mixing (a) the metal oxide coated with a silicone and/or fluorine compound, (b) the monomer component (vinyl monomers having a solubility parameter of less than about 8.9, including monomer components having a solubility parameter of less than about 8.9, and (c) the crosslinking agent and a second step (hereinafter referred to as a step 2) of suspension-polymerizing the resultant mixture.

As to the ratio by weight of the metal oxide coated with a silicone and/or fluorine compound, the monomer component (including vinyl monomers having a solubility parameter of less than about 8.9 and optionally monomer components having a solubility parameter of not less than about 8.9) to the crosslinking agent in step 1, the ratio by weight of metal oxide/the sum of all the monomer components and the crosslinking agent is preferably from 25/75 to 90/10 and more preferably from 30/70 to 70/30.

For the dispersion of the vinyl monomer, an organic solvent may be added according to the need to improve dispersion efficiency. Examples of such organic solvents include straight-chain or cyclic saturated hydrocarbon type solvents (e.g., n-pentane, n-hexane, n-heptane, n-octane, n-nonane, n-decane and cyclohexane), straight-chain or cyclic unsaturated hydrocarbon type solvents (e.g., toluene and xylene), ketone type organic solvents (e.g., acetone and methyl ethyl ketone), ester type organic solvents (e.g., ethyl acetate and butyl acetate) and straight-chain or cyclic polydimethylsiloxanes.

Here, for the dispersion, a dispersing machine such as a homogenizer, pressure homogenizer, ultrasonic dispersing machine, attritor mill, ball mill or sand mill may be used.

A dispersion/emulsion agent to be added in step 2 may be added in step 1 according to the need. When added, the dispersion/emulsion agent is preferably added in an amount of from 1 to 30% by weight based on 100% by weight of the metal oxide. The time required for dispersion is preferably about from 30 minutes to 5 hours.

In step 2, the dispersion solution obtained in step 1, water, a polymerization initiator and a dispersion/emulsion agent are preferably mixed, emulsified or suspended and then polymerized.

Examples of the dispersion/emulsion agent for suspension polymerization include low-molecular weight surfactants such as anionic surfactants, e.g., sodium laurylsulfate, sodium cetylsulfate, sodium polyoxyethylene lauryl ether sulfate, sodium fatty acid salt and sodium alkyl(methyl) taurate and other cationic surfactants and nonionic surfactants; high-molecular weight dispersants such as polyvinyl alcohols, polyvinylpyrrolidones, hydroxyethyl cellulose, hydroxypropyl cellulose, gelatins, starch, carboxymethyl cellulose and polyvinyl alkyl ether; and inorganic salts which are sparingly soluble in water such as barium sulfate, potassium sulfate, barium carbonate, calcium carbonate, magnesium carbonate and calcium phosphate. The dispersion/emulsion agent is preferably added in an amount of from 0.1 to 20% by weight based on 100% by weight of the dispersion solution obtained in step 1.

Examples of polymerization initiators include peroxide type initiators, organic or inorganic peroxides or their salts and redox types which are single azobis types or combinations of azobis types and reducing agents, although depending on the reaction system.

Given as examples of these redox types are combinations of t-butyl peroxide, t-amyl peroxide, cumyl peroxide, acetyl peroxide, propionyl peroxide, benzoyl peroxide (BPO), benzoylisobutyryl peroxide, lauroyl peroxide (LPO), t-butyl hydroperoxide, cyclohexyl hydroperoxide, tetraphosphorous hydroperoxide, t-butyl peracetate, t-butyl perbenzoate, bis(2-ethylhexyl peroxydicarbonate), 2,2'-azobisisobutyronitrile) (AIBN), 2,2'-azobisisovaleronitrile, 2,2'-azobis(2-methylbutyronitrile), phenylazotriphenylmethane, 2,2'-azobis(2-amidinopropane)dihydrochloride, 2,2'-azobis[2(5-methyl-2-imidazoline-2-yl)propane]dihydrochloride, 2,2'-azobis[2-(2-imidazoline-2-yl)propane]dihydrochloride, sodium persulfate, potassium persulfate, ammonium persulfate, hydrogen peroxide or persulfate with a tertiary amine such as triethylamine, triethanolamine or dimethylaniline.

The amount of the polymerization initiator is preferably from 0.1 to 5% by weight based on the total amount of the vinyl monomer, or based on the sum total amount of all the monomers, and the crosslinking agent. The polymerization initiation temperature is preferably from 20 to 95° C. and the time required for polymerization is preferably from 3 to 48 hours.

As aforementioned, the metal oxide coated with a silicone and/or fluorine compound, the monomer components comprising a vinyl monomer having a solubility parameter of less than about 8.9 and the crosslinking agent are dispersed or suspended in water according to known methods to form liquid droplets which are then made to enter into a polymerization reaction, whereby an intended polymer composite particle can be produced.

After the polymerization is finished, the polymer composite particle is subjected to solid-liquid separation using filtration, centrifugation or the like, the water phase is removed and the oil phase is washed with water according to the need. Then, the polymer composite particle is treated by the usual method such as drying under reduced pressure, spraying drying, or freeze drying, whereby the polymer composite can be isolated as a powder. Also, separation of the aggregate into smaller particles may be carried out according to the need. As a method of separation, a drying method using a jet mill, pin mill, co-mill, hammer mill, feather mill or the like or a wet method using a line mixer, disperser, homogenizer, milder, homomixer or the like may be used.

[Fine Particle Metal Oxide (A)]

Among three kinds of powders which may be used for the ultraviolet protection cosmetic of the present invention, the first powder is a microparticle metal oxide (hereinafter referred to as a microparticle oxide) having an ability to protect from ultraviolet rays and visible-light transmittance and an average primary particle diameter of from 0.001 to 0.1 μm. Here, the primary particle has a preferred shape including an elliptic form besides a pearl form, and also includes those being convex and concave on the surface and in which the ratio of the major diameter to minor diameter of the particle is 3 or less when it has no pearl form. Also, the term "having an ability to protect from ultraviolet rays" or a "highly effective ultraviolet protection" as used herein means that the microparticle metal oxide has the effect of absorbing or scattering ultraviolet rays having a wavelength range of from 280 to 400 nm, particularly, UVB and UVAII having a wavelength range of from 280 to 340 nm. Moreover, the term "having visible-light transmittance" as used herein means that when applying a dispersion solution, prepared by dispersing 5% by weight of the powder in silicone, to the skin in a coating amount of 1 mg/cm$^2$, the solution has transparency without any white residue. Preferably, the solution has transparency without any white residue even in the case of a silicone dispersion solution comprising 10% by weight of the powder.

The average particle diameter of the primary particle of the microparticle oxide is designed to be preferably 0.001 μm or more, more preferably 0.005 μm or more and even more preferably 0.01 μm or more from the viewpoint of the feeling in use when a cosmetic is applied. Also, the average particle diameter is designed to be preferably 0.1 μm or less, more preferably 0.08 μm or less and even more preferably 0.06 μm or less from the viewpoint of transparency when a cosmetic is applied. Incidentally, the average particle diameter in the present invention means an average of particle diameters measured from an electron microphotograph.

The microparticle oxide of the present invention is a metal oxide having the effect of absorbing and scattering ultraviolet rays ranging widely from UVB to UVAII. Particularly, the microparticle oxide is preferably one or more types selected from zinc oxide, titanium oxide and cerium oxide, including mixtures thereof, from the point that these metal oxides have absorbing and scattering effects of high ultraviolet rays.

Examples of commercially available products of the microparticle oxide include FINEX-25, FINEX-50 and FINEX-75 (the above products are manufactured by Sakai Chemical Industry Ltd.); and MZ500 series and MZ700 series (the above products are manufactured by TAYCA Corp.) and ZnO-350 (the above product is manufactured by Sumitomo Osaka Cement Co., Ltd) as microparticle zinc oxide. Also, TTO-55 series and TTO-51 series (the above products are manufactured by Ishihara Sangyo Kaisha Ltd.) and JR series and JA series (the above products are manufactured by TAYCA Corp., Ltd) are exemplified as examples of microparticle titanium oxide. Also, high purity cerium oxides commercially available from Nikki corporation or Seimi Chemical corporation are also given as examples of microparticle cerium oxide. Among these products, products made of zinc oxide or titanium oxide are particularly preferable.

Regarding the surface of the microparticle oxide, it is preferable to use microparticle oxides surface-treated in the same manner as in the case of usual cosmetic powders to improve dispersibility in a cosmetic and to improve the ability to protect from ultraviolet rays and have improved transparency of the microparticle oxide.

Examples of surface treating methods include treatments using methyl hydrogen polysiloxane, dimethylpolysiloxane, silicone resins or the like, treatments using surfactants such as anionic surfactants and cationic surfactants, treatments using polymers such as nylon, polymethylmethacrylate, polyethylene, Teflon® or polyamino acid and treatments using a perfluoro group-containing compound, lecithin, collagen, metal soap, lipophilic wax or partially esterified product or completely esterified product of polyhydric alcohols.

The throughput of the microparticle oxide is preferably designed to be from 0.1 to 20% by weight and preferably from 1 to 10% by weight based on the microparticle oxide from the viewpoint of having an ability to protect from ultraviolet rays.

Further, the microparticle oxide may be provided in any state such as a powder, oil dispersion and water dispersion as far as the particle is well-dispersed when formulated in a cosmetic. When the microparticle oxide is formulated in the state of an oil dispersion or a water dispersion, it is preferable to use a dispersion in which a microparticle oxide powder is highly dispersed because the ultraviolet protection effect and visible-light transmittance are improved with the result that the ultraviolet protection effect and transparency of a cosmetic are improved. It is therefore desirable to use a high dispersion of these microparticle oxides (hereinafter referred to as a microparticle high dispersion) or a combination of the microparticle high dispersion and a powdery microparticle oxide.

Examples of the microparticle high dispersion include super-microparticle dispersions as described in, for example, the publication of JP-A No. 8-12961, the publication of JP-A No. 9-100112, the publication of JP-A No. 11-131048 and the publication of JP-A No. 2000-290156.

[Flake Zinc Oxide (B)]

Among the powders different in shape which may be used for the cosmetic having an ability to protect from ultraviolet rays of the present invention, the second powder is a flake zinc oxide having an average size of from 0.1 µm to 1 µm and an average thickness of from 0.01 µm to 0.2 µm. The use of the flake zinc oxide brings about a high scattering effect in, particularly among long wavelengths UVAl (340 nm to 400 nm), so that a good ability to protect from ultraviolet rays is produced.

Here, the average size and average thickness of the flake zinc oxide are an average particle diameter and average thickness in an area direction which are measured from an electron microphotograph.

The average size is designed to be preferably 0.1 µm or more from the viewpoint of preventing the occurrence of aggregation leading to a reduction in dispersibility and preferably 1 µm or less from the viewpoint of high transparency and ultraviolet rays absorbing ability. The average size is more preferably from 0.1 µm to 0.8 µm and even more preferably from 0.2 µm to 0.7 µm. The average thickness is designed to preferably be 0.01 µm or more from the viewpoint of a resistance to the collapse of the flake shape and more preferably 0.2 µm or less from the viewpoint of a good feeling in use. The average thickness is more preferably from 0.01 µm to 0.1 µm and even more preferably from 0.01 µm to 0.05 µm.

The aspect ratio of the flake zinc oxide is preferably 3 or more, more preferably 5 or more and even more preferably 7 or more from the viewpoint of improving transparency. Here, the aspect ratio means a value found from the ratio of (average size/average thickness).

As the flake zinc oxide of the present invention, flake zinc oxide improved in transparency is preferably compounded together with a metal element having two or more valences in an amount of 0.005 to 1.0 mol based on 100 mol of zinc. The metal element having two or more valences may be preferably combined with the flake zinc oxide so that it may be bound or held on the surface or in the inside of the flake zinc oxide being the mother particle.

Examples of the metal element having two or more valences may include iron, zirconium, calcium, germanium, manganese, magnesium and yttrium. These elements may be used either alone or in combination. Among these elements, iron, zirconium and magnesium are preferable from the view point of having a highly effective ultraviolet protection ability. Also, when using these metal elements by combining them, combinations of zirconium and iron, zirconium and magnesium, iron and magnesium, iron and calcium and magnesium and germanium are preferable.

The amount of the metal element having two or more valences is designed to be 0.005 mol or more and more preferably 0.01 mol or more based on 100 mol of zinc contained in the flake zinc oxide powder from the viewpoint of ultraviolet protection ability. Also, the amount of the metal element is 1.0 mol or less and more preferably 0.5 mol or less from the viewpoint of a good ability to protect from ultraviolet rays. It is to be noted that the content of the metal element having two or more valences may be determined by dissolving the powder in an acid or alkali solution which dissolves the metal elements contained in the powder, followed by measuring using IPC emission analysis.

As to the surface of the flake zinc oxide, it is preferable to use flake zinc oxide which has been surface-treated to improve dispersibility in the cosmetic. As the surface treating method, the above methods used for the surface treatment of the microparticle oxide maybe used. The throughput of the surface treating agent used for the flake zinc oxide is preferably designed to be from 0.1 to 20% by weight and more preferably from 1 to 10% by weight based on the flake zinc oxide from the viewpoint of having a good ability to protect from ultraviolet rays.

Examples of the flake zinc oxide used in the present invention include flake zinc oxides described in the publication of JP-A No. 1-175921, the publication of JP-A No. 1-230431, the publication of JP-A No. 8-12526 and the publication of JP-A No. 9-137152.

[Cosmetic]

As to cosmetics which may be formulated using the polymer composite particle of the present invention, any usual cosmetic may be formulated with the polymer composite particle as far as it can produce a UV-shutting effect or skin-concealing effect. Specifically, makeup cosmetics such as foundations, cheek rouges, eye shadows, mascaras, eye liners, eyebrows, lipsticks and nail enamels, sunscreen cosmetics and base cosmetics are desirable. The content of the polymer composite particle in the cosmetic is preferably from 0.1 to 60% by weight mass and more preferably from 1 to 40% by weight based on the cosmetic composition.

Further, in the cosmetic, other components which may be used as usual cosmetic raw materials, for example, white pigments (e.g., titanium oxide), extender pigments (e.g., mica, talc, sericite and barium sulfate), color pigments (e.g., red iron oxide, yellow iron oxide, black iron oxide, Yellow No. 401, Red No. 226, capsulated color pigments and organic dyes), pearl pigments, natural minerals, organic powders, oil agents (e.g., vaseline, lanolin, ceresin, olive oil, jojoba oil, castor oil, squalane, liquid paraffin, ester oils, diglyceride, triglyceride, silicone oil, perfluoropolyether and fluorine modified silicone oil), ultraviolet protection agents, gelling agents, waxes (e.g., solid or semi-solid oils such as microcrystalline waxes, higher fatty acids and higher alcohols), metal soaps, surfactants, humectants, antiseptics, perfumes, thickeners, antioxidants, disinfectants, antiperspirants and other various additives may be appropriately selected and used in formulating.

The cosmetic of the present invention may be used in the form of a solid cosmetic, wax cosmetic, emulsion (O/W, W/O) cosmetic, liquid cosmetic, gel cosmetic and the like.

In the present invention, as to the compounding ratio of the total amount of the microparticle metal oxides contained in the polymer composite particle embracing a first microparticle metal oxide and a third microparticle metal oxide to a second flake zinc oxide, the ratio by mass of the second flake zinc oxide to the total amount of the microparticle metal oxides is preferably from 0.05 to 0.4 and more preferably from 0.05 to 0.2 from the viewpoint of the balance between a sufficient UVA protection effect and the securance of sufficient transparency as a cosmetic without intensifying whiteness when the cosmetic is applied.

As mentioned above, the use of a combination of the microparticle metal oxide having an almost granular particle shape, the ability of protecting from ultraviolet rays extending widely from UVB to UVAII and having visible-light transmittance, the use of a zinc oxide having a flake form and the high effect of scattering light ranging from UVAII to UVAI close to visible light and the microparticle metal oxide contained in a polymer composite particle makes it possible to improve protection from ultraviolet rays with high efficiency and to obtain a cosmetic superior in transparency and a good feeling in use.

In the cosmetic of the present invention, the ability to protect from ultraviolet rays can be further improved by preferably adding an organic ultraviolet absorber. No particular limitation is imposed on the type of organic ultraviolet absorber to be used and any of oil-soluble type absorbers and water-soluble type absorbers may be preferably used.

The amount of the ultraviolet absorber in the cosmetic, though it differs depending on its preparation form and the like, is preferably from 0.1 to 25.0% by weight and more preferably from 0.5 to 10.0% by weight, by weight of the cosmetic composition from the viewpoint of improving the ability to protect from ultraviolet rays. If the amount of the ultraviolet absorber to be formulated falls in the above range, the ability to protect from ultraviolet rays is improved sufficiently, oily feeling is not enhanced and a good feeling in use is obtained, which is preferable.

Also, components used in usual cosmetics may be used in the cosmetic of the present invention, including, for example, liquid oils, solid fats (waxes), semi-solid oils, alcohols, water, humectants, water-soluble polymers, oil-soluble polymers, high-molecular latexes, various surfactants, chemicals, vegetable extracts, ceramides, hematogenic promoters, frigid agents, antiperspirant agents, disinfectants, dermal activators, pH regulators, thickeners, antioxidants, antiseptics and perfumes.

The cosmetic of the present invention can be used as various cosmetics, such as skin care cosmetics, makeup cosmetics and hair cosmetics. Examples of the preparation form used in the present invention include a powder form, powdery solid form, oil-in-water type emulsion form, lotion form, oily solid form, paste form, multilayer form and gel form. Particularly, examples of make-up cosmetics include sunscreen cosmetics, foundations, white powders, cosmetic bases, rouges, lipsticks, concealers, and eye products.

Although not wanting to be limited by theory, in order for the cosmetic to exhibit highly effective ultraviolet protection, it is necessary to fulfill two conditions that the metal oxide is contained in a considerably effective amount and uniformly dispersed in the polymer composite particle and that the polymer composite particle is uniformly dispersed in the formulated composition. Generally, when a metal oxide whose surface is untreated is compounded in a high concentration, it absorbs a monomer and hence loses its fluidity, with the result that it cannot be emulsified. In preferred embodiments of the present invention, on the contrary, the metal oxide having an average particle diameter of 1 µm or less and coated with a silicone and/or fluorine compound and the monomer having a solubility parameter less than about 8.9 are used whereby a considerable amount of the metal oxide can be dispersed relatively uniformly in the polymer composite particle, bringing about good fluidity, enabling emulsification. Also, because the polymer composite particle can be compounded stably in the cosmetic, the cosmetic compounded of the polymer composite particle has a highly effective ultraviolet protection ability and a good feeling in use.

The preferred cosmetic of the present invention uses a combination of a microparticle metal oxide having a specific average particle diameter, has the effect of protection from ultraviolet rays ranging from UVB to UVAII and visible light transmittance, uses a flake zinc oxide having a high effect of scattering light ranging from UVAII to UVAI close to visible light, uses a microparticle metal oxide contained in a polymer composite particle which has a high UV protective effect, has a good feeling in use, and has a specific particle diameter, whereby the cosmetic has a highly effective ultraviolet protection ability, particularly, with respect to the effect of protecting from ultraviolet rays having long wavelengths, has a high transparency and a good feeling in use.

EXAMPLE

The following examples further describe and demonstrate embodiments of the present invention. The examples are given solely for the purpose of illustration and are not to be construed as limitations of the present invention.

Example 1

Using a beads mill, 60 g of silicone-treated zinc oxide (MZ-507S) manufactured by Teika was stirred in 45 g of laurylmethacrylate (SP value: 8.7) and 45 g of ethylene glycol dimethacrylate for 3 hours (the average particle diameter of zinc oxide which was measured by ELS-8000 manufactured by Otsuka Electronics Co., Ltd.: 0.3 µm). Thereafter, 3 g of lauroyl peroxide was added to the slurry. 20 g of sodium laurylsulfate was dissolved in 1500 g of ion exchange water and the mixture was added to the above zinc oxide slurry, which was then dispersed using a milder (the average particle diameter of the emulsion which was measured by LA-910 manufactured by Horiba, Ltd.: 1.6 µm). Next, the dispersion solution was placed in a 2000 mL separable flask. After the atmosphere in the flask was replaced by nitrogen, the dispersion solution was raised to 70° C. while stirring at 200 r/min to run polymerization at 70° C. for 10 hours, and the resulting solution was raised to 80° C. to run polymerization at 80° C. for 10 hours in a nitrogen atmosphere. After the polymerization was finished, the resulting reaction solution was subjected to centrifugation to collect solids, which were then washed with water, freeze-dried and then pulverized using a jet mill to obtain 120 g of a polymer composite particle (particle diameter: 2 µm and ratio of zinc oxide included: 40% by weight)

Figure 2:
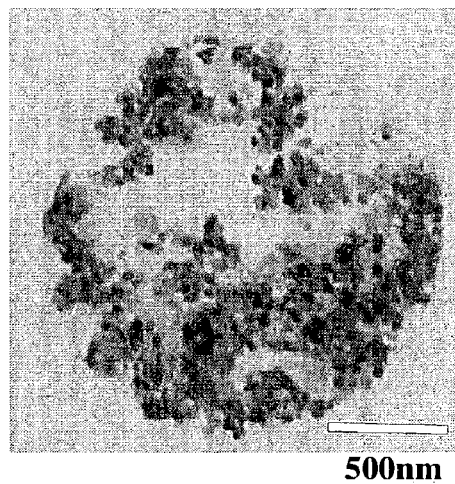
FIG. 2 is a transmission type electron microphotograph of a polymer composite particle obtained in Example 1.

FIG. 1 and FIG. 2 show a scanning type electron microphotograph and a transmission type electron microphotograph of the resulting polymer composite particle respectively.

Example 2

Using a beads mill, 90 g of silicone-treated zinc oxide (MZ-507S) manufactured by TAYCA CORP. was stirred in 45 g of stearylmethacrylate (SP value: 8.7), 45 g of 1,6-hexanedioldimethacrylate and 30 g of heptane for 3 hours (the average particle diameter of zinc oxide which was measured by ELS-8000 manufactured by Otsuka Electronics Co., Ltd.: 0.4 µm). Thereafter, 3 g of lauroyl peroxide was added to the slurry. 15 g of sodium cocoylmethyltaurine was dissolved in 1500 g of ion exchange water and the mixture was added to the above zinc oxide slurry, which was then dispersed using a homogenizer (the average particle diameter of the emulsion which was measured by LA-910 manufactured by Horiba, Ltd.: 1.6 µm). Next, the dispersion solution was placed in a 2000 mL separable flask. After the atmosphere in the flask was replaced by nitrogen, the dispersion solution was raised to 70° C. while stirring at 200 r/min to run polymerization at 70° C. for 10 hours, and the resulting solution was raised to 80° C. to run polymerization at 80° C. for 10 hours in a nitrogen atmosphere. After the polymerization was finished, the resulting reaction solution was subjected to centrifugation to collect solids, which were then washed with water, freeze-dried and then pulverized using a jet mill to obtain 120 g of a polymer composite particle (ratio of zinc oxide included: 50% by weight)

Example 3

Using a beads mill, 40 g of silicone-treated zinc oxide (MZ-507S) manufactured by TAYCA CORP. was stirred in 30 g of laurylmethacrylate (SP value: 8.7) and 30 g of ethylene glycol dimethacrylate for 3 hours (the average particle diameter of zinc oxide which was measured by ELS-8000 manufactured by Otsuka Electronics Co., Ltd.: 0.3 µm). Thereafter, 1.5 g of 2,2'-azobis-2,4-dimethylvaleronitrile was added to the slurry. 30 g of polyvinyl alcohol (GE30, manufactured by The Nippon Synthetic Chemical Industry Co., Ltd.) and 1 g of sodium stearoylmethyltaurine were dissolved in 500 g of ion exchange water and the mixture was added to the above zinc oxide slurry, which was then dispersed using a milder (the average particle diameter of the emulsion which was measured by LA-910 manufactured by Horiba, Ltd.: 2.0 µm). Next, the dispersion solution was placed in a 1000 mL separable flask. After the atmosphere in the flask was replaced by nitrogen, the dispersion solution was raised to 60° C. while stirring at 200 r/min to run polymerization at 60° C. for 2 hours, and the resulting solution was raised to 80° C. to run polymerization at 80° C. for 4 hours in a nitrogen atmosphere. After the polymerization was finished, the resulting reaction solution was subjected to centrifugation to collect solids, which were then washed with water, freeze-dried and then pulverized using a jet mill to obtain 90 g of a polymer composite particle (ratio of zinc oxide included: 40% by weight)

Example 4

Using a beads mill, 50 g of silicone-treated titanium oxide (obtained by processing titanium oxide having an average particle diameter of 0.25 µm (CR-50, manufactured by Ishihara Sangyo Kaisha, Ltd.) by water-repellent treatment using methyl hydrogen polysiloxane (2% by weight based on titanium oxide)) was stirred in 56 g of laurylmethacrylate (SP value: 8.7) and 19 g of ethylene glycol dimethacrylate for 3 hours (the average particle diameter of titanium oxide which was measured by ELS-8000 manufactured by Otsuka Electronics Co., Ltd.: 0.3 µm). Thereafter, 1.5 g of lauroyl peroxide was added to the slurry. 7.5 g of polyvinyl alcohol (EG-30, manufactured by The Nippon Synthetic Chemical Industry Co., Ltd.) was dissolved in 750 g of ion exchange water and the mixture was added to the above titanium oxide slurry, which was then dispersed using a homogenizer (the average particle diameter of the emulsion which was measured by LA-910 manufactured by Horiba, Ltd.: 11.5 µm). Next, the dispersion solution was placed in a 2000 mL separable flask. After the atmosphere in the flask was replaced by nitrogen, the dispersion solution was raised up 75° C. while stirring at 150 r/min to run polymerization at 75° C. for 8 hours in a nitrogen atmosphere. After the polymerization was finished, the resulting reaction solution was subjected to centrifugation to collect solids, which were then washed with water, freeze-dried and then pulverized using a jet mill to obtain 120 g of a polymer composite particle (ratio of titanium oxide included: 40% by weight)

Example 5

Using a beads mill, 50 g of silicone-treated titanium oxide (obtained by processing titanium oxide having an average particle diameter of 0.25 µm (CR-50, manufactured by Ishihara Sangyo Kaisha Ltd.) by water-repellent treatment using methyl hydrogen polysiloxane (2% by weight based on titanium oxide)) was stirred in 10 g of polydimethyl siloxypropyl methacrylate (Silaplane FM0711, manufactured by Chisso Corporation, MW: 1000, SP value: 7.6), 50 g of isostearyl methacrylate (SP value: 8.2), 40 g of ethylene glycol dimethacrylate and 10 g of polydimethylsiloxane (5000 cs) for 3 hours (the average particle diameter of titanium oxide which was measured by ELS-8000 manufactured by Otsuka Electronics Co., Ltd.: 0.4 µm). Thereafter, 3 g of lauroyl peroxide was added to the slurry. 45 g of polyvinyl alcohol (EG-30, manufactured by The Nippon Synthetic Chemical Industry Co., Ltd.) was dissolved in 1500 g of ion exchange water and the mixture was added to the above titanium oxide slurry, which was then dispersed using a homogenizer (the average particle diameter of the emulsion which was measured by LA-910 manufactured by Horiba, Ltd.: 1.8 µm). Next, the dispersion solution was placed in a 2000 mL separable flask. After the atmosphere in the flask was replaced by nitrogen, the dispersion solution was raised to 70° C. while stirring at 200 r/min to run polymerization at 70° C. for 10 hours and then raised to 80° C. to run polymerization for 10 hours in a nitrogen atmosphere. After the polymerization was finished, the resulting reaction solution was subjected to centrifugation to collect solids, which were then washed with water, freeze-dried and then pulverized using a jet mill to obtain 120 g of a polymer composite particle (ratio of titanium oxide included: 31% by weight)

Comparative Example 1

Using a beads mill, 60g of silicone-treated zinc oxide (MZ-507S) manufactured by TAYCA CORP. was stirred in 60 g of styrene (SP value: 9.2) and 30 g of divinylbenzene for 3 hours (the average particle diameter of zinc oxide which was measured by ELS-8000 manufactured by Otsuka Electronics Co., Ltd.: 0.3 µm). Thereafter, 3 g of lauroyl peroxide was added to the slurry. 20 g of sodium laurylsulfate was dissolved in 1500 g of ion exchange water and the mixture was added to the above zinc oxide slurry, which was then dispersed using a milder (the average particle diameter of the emulsion which was measured by LA-910 manufactured by Horiba, Ltd.: 2.1 µm). Next, the dispersion solution was placed in a 2000 mL separable flask. After the atmosphere in the flask was replaced by nitrogen, the dispersion solution was raised to 70° C. while stirring at 200 r/min to run polymerization at 70° C. for 10 hours, and the resulting solution was raised to 80° C. to run polymerization at 80° C. for 10 hours in a nitrogen atmosphere. After the polymerization was finished, the resulting reaction solution was subjected to centrifugation to collect solids, which were then washed with water, freeze-dried and then pulverized using a jet mill to obtain 110 g of a polymer composite particle (ratio of zinc oxide included: 40% by weight)

Figure 3:
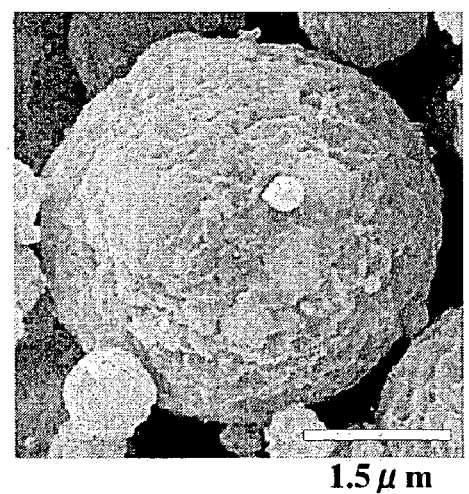
FIG. 3 is a scanning type electron microphotograph of a polymer composite particle obtained in Comparative Example 1.
Figure 4:
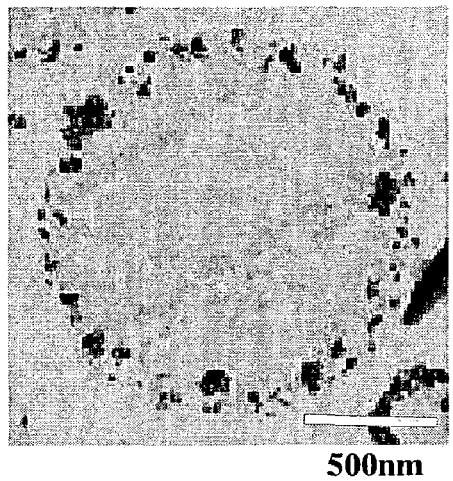
FIG. 4 is a transmission type electron microphotograph of a polymer composite particle obtained in Comparative Example 1.

FIG. 3 and FIG. 4 show a scanning type electron microphotograph and a transmission type electron microphotograph of the resulting polymer composite particle respectively.

Comparative Example 2

Using a beads mill, 30 g of silicone-treated zinc oxide (MZ-507S) manufactured by TAYCA Corp. was stirred in 70 g of methylmethacrylate (SP value: 8.9) for 3 hours (the average particle diameter of zinc oxide which was measured by ELS-8000 manufactured by Otsuka Electronics Co., Ltd.: 0.3 µm). Thereafter, 2.1 g of lauroyl peroxide was added to the slurry. 5 g of sodium laurylsulfate was dissolved in 500 g of ion exchange water and the mixture was added to the above zinc oxide slurry, which was then dispersed using a milder (the average particle diameter of the emulsion which was measured by LA-910 manufactured by Horiba, Ltd.: 2.2 µm) Next, the dispersion solution was placed in a 2000 mL separable flask. After the atmosphere in the flask was replaced by nitrogen, the dispersion solution was raised to 70° C. while stirring at 200 r/min to run polymerization at 70° C. for 10 hours, and the resulting solution was raised to 80° C. to run polymerization at 80° C. for 10 hours in a nitrogen atmosphere. After the polymerization was finished, the resulting reaction solution was subjected to centrifugation to collect solids, which were then washed with water, freeze-dried and then pulverized using a jet mill to obtain 70 g of a polymer composite particle (ratio of zinc oxide included: 30% by weight).

Figure 5:
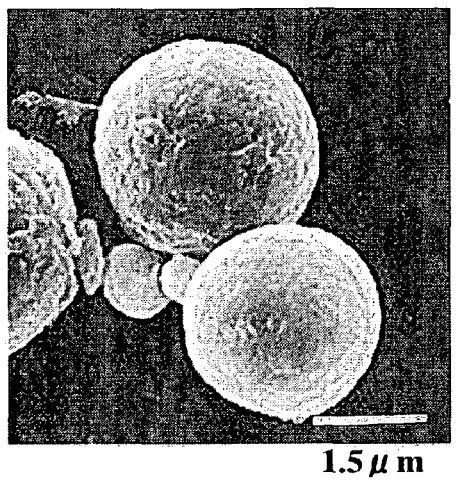
FIG. 5 is a scanning type electron microphotograph of a polymer composite particle obtained in Comparative Example 2.
Figure 6:
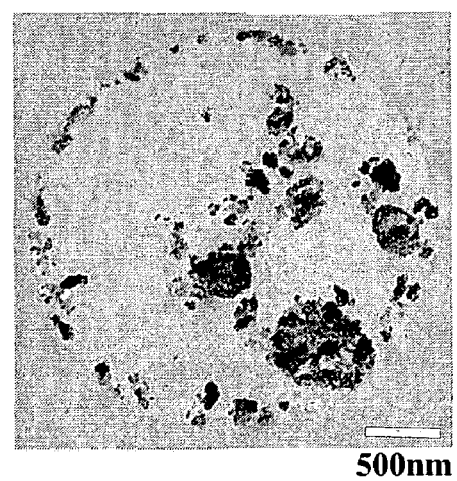
FIG. 6 is a transmission type electron microphotograph of a polymer composite particle obtained in Comparative Example 2.

FIG. 5 and FIG. 6 show a scanning type electron microphotograph and a transmission type electron microphotograph of the resulting polymer composite particle respectively.

Comparative Example 3

Using a beads mill, 20g of zincoxide (MZ-700: particle diameter shown in a catalogue: 0.02 µm, silicone-untreated product) manufactured by TAYCA Corp. was stirred in 40 g of laurylmethacrylate (SP value: 8.7), 40 g of ethylene glycol dimethacrylate and 20 g of heptane for 3 hours. Thereafter, 1.6 g of 2,2'-azobis-2,4-dimethylvaleronitrile was added to the slurry. 6.5 g of sodium laurylsulfate was dissolved in 500 g of ion exchange water and the mixture was added to the above zinc oxide slurry, which was then dispersed using a milder (the average particle diameter of the emulsion which was measured by LA-910 manufactured by Horiba, Ltd.: 2.0 µm). Next, the dispersion solution was placed in a 1000 mL separable flask. After the atmosphere in the flask was replaced by nitrogen, the dispersion solution was raised to 60° C. while stirring at 200 r/min to run polymerization at 60° C. for 2 hours, and the resulting solution was raised to 80° C. to run polymerization at 80° C. for 4 hours in a nitrogen atmosphere. After the polymerization was finished, the resulting reaction solution was subjected to centrifugation to collect solids, which were then washed with water, freeze-dried and then pulverized using a jet mill to obtain 70 g of a polymer composite particle (ratio of zinc oxide included: 20% by weight).

Test Example 1

With regard to the polymer composite particles obtained in Examples 1 to 5 and Comparative Examples 1 to 3, the SPF of each polymer composite particle was measured using the following method. Also, the blending characteristics of each polymer composite particle in a product and a feeling in use were evaluated using the following method. The results are shown in Table 1.

<Method of Measuring SPF>

Formulation

1. Silicone modified with polyether (SH3775M, manufactured by Toray Dow Corning Silicone Co., Ltd.): 1.8% by weight
2. Neopentyl glycol dicaprate: 2.0% by weight
3. Squalane: 4.0% by weight
4. 2-Ethylhexyl 4-methoxycinnamate: 1.0% by weight
5. Straight-chain dimethylsilicone (2 cs): 36.0% by weight
6. Polymer composite particle: 5.0% by weight as a metal oxide
7. Glycerol: 4.3% by weight
8. Water: balance Procedures a) Components 1 to 4 are combined uniformly and a dispersion solution of components 5 and 6 is added to the mixture for further dispersion.
b) Components 7 and 8 are mixed.
c) Mixture b) is added to Mixture a) gradually and the resulting mixture is subjected to a homomixer to make an emulsion.

Preparation of a Sample

A medical tape (Transpore surgical tape) is prepared. 80 µL of the aforementioned emulsion is placed on the tape having 5×8 cm$^2$ in size by using a syringe and spread over the entire surface using fingers.

Measurement of SPF

The aforementioned sample is set to a simplified type SPF analyzer meter (UV TRANSMITTANCE ANALYZER, manufactured by labsphere) to measure. The sample is measured five times to calculate an average which is adopted. (rounding numbers off to the first digit)

<Evaluation of Blending Characteristics in a Product and Feeling in Use>

The blending characteristics in a product was evaluated by rating the same formulated composition that was used for the aforementioned measurement of SPF as to the preserving stability for one month according to the following standard of three stages. Also, the feeling in use was evaluated by rating the same formulated composition that was used for the aforementioned measurement of SPF as to feel to the touch according to the following standard of three stages by one expert panelist.

Blending Characteristics (Preserving Stability for one Month)
○: Almost no coagulation is observed.
Δ: Coagulation is observed a little.
X: Coagulation is observed significantly.

Feeling in Use
○: Usable without a sense of incongruity.
Δ: Somewhat rough feeling is felt.
X: Rough feeling is felt.

TABLE 1

|  | SPF | Blending characteristics in a product | Feeling in use |
|---|---|---|---|
| Example 1 | 7 | ○ | ○ |
| Example 2 | 7 | ○ | ○ |
| Example 3 | 7 | ○ | ○ |
| Example 4 | 7 | ○ | ○ |
| Example 5 | 7 | ○ | ○ |
| Comparative example 1 | 4 | ○ | ○ |
| Comparative example 2 | 4 | ○ | ○ |
| Comparative example 3 | 4 | Δ | ○ |

Test Example 2

Emulsions having the compositions shown in Table 2 were produced according to the present invention and for comparison to evaluate SPF and feeling in use by using the following method. The results are shown in Table 2.

<Method of Measuring SPF>

Each sample was evaluated in the same manner as in the preparation of a sample and the measurement of SPF as described in Test Example 1.

<Method of Evaluating a Feeling in Use>

Each of the emulsions of the present invention and the comparative emulsions was applied to the back of each hand of ten expert panelists to evaluate feel to the touch (amount to be applied: each sample was applied so as to form a circle having a diameter of 2 cm on the back of the hand when it was taken out of a container). Each sample was evaluated in three stages rated as "good", "undefined whether it is good or not" and "bad", and each case of "good", "undefined whether it is good or not" and "bad" is rated as 1 point, 0.5 points and 0 points respectively to express the total points of the aforementioned ten expert panelists.

TABLE 2

|  | Embodiment of the present invention | Comparative product |
|---|---|---|
| Emulsion (% by mass) | | |
| Silicone KF-6015 (manufactured by Shin-Etsu Chemical Co., Ltd) | 1.2 | 1.2 |
| Silicone KF-96A(2cs) (manufactured by Shin-Etsu chemical Co. ,Ltd) | 43.6 | 43.6 |
| 2-Ethylhexyl paramethoxycinnamate | 5.0 | 5.0 |
| Complex polymer particle of example 1 | 20.0 | — |
| zinc oxide MZ-507S (manufactured by Teika) | — | 8 |
| 86% glycerol | 2.0 | 2.0 |
| 95 degree synthetic alcohol | 8.0 | 8.0 |
| Purified water | 20.2 | 32.2 |
| Total | 100.0 | 100.0 |

TABLE 2-continued

|  | Embodiment of the present invention | Comparative product |
|---|---|---|
| Results of evaluation | | |
| SPF | 24 | 15 |
| Feeling in use (point) | 7.5 | 3 |

Examples 6 and 7 and Comparative Examples 4 to 8

(Method of Evaluation)
(1) Ultraviolet Protection Effect
The SPF value of the cosmetic was measured using an SPF analyzer (Optometrics corporation) and expressed according to the following standard.

[Standard for Evaluating a UVB Protective Effect]:
○: SPF value is 35 or more.
Δ: SPF value is 30 or more and less than 35.
X: SPF value is less than 30.

[Standard for evaluating a UVA protective effect]:
○: T(UVA) is less than 18%.
Δ: T(UVA) is 18% or more and less than 20%.
X: T(UVA) is 20% or more.

Here, T(UVA) is defined by the following equation:

$$T(UVA)(\%) = \sum_{320}^{400} T\lambda \times \Delta\lambda \bigg/ \sum_{320}^{400} \Delta\lambda$$

where:
Tλ: transmittance at a wavelengthλ (%) and Δλ: interval between measured wavelengths (2) Transparency (Whiteness when a Cosmetic is Applied)
Using an SPF analyzer (Optometrics corporation), a whole transmission light spectrum was measured to show the whiteness of each sample from a transmittance at a wavelength of 450 nm according to the following standard.
○: T(450 nm) is 55% or more.
Δ: T(450 nm) is 45% or more and less than 55%.
X: T(450 nm) is less than 45%.

(3) Feeling in Use
Each cosmetic was evaluated as to feeling in use when the cosmetic was applied in three stages rated as follows: comfortable without any frictional feel: 3 points, somewhat frictional feel and sticky feel are felt: 2 points and frictional feel and sticky feel are felt: 1 point, by five expert panelists and an average of each rating of the five panelists was rated according the following standard.

<Standard of Evaluation>
○: 2.8 points or more.
Δ: 2.5 points or more.
X: Less than 2.5 points.

Example 6, 7 and Comparative Example 4 to 8

A liquid ultraviolet protection cosmetic having the composition shown in Table 3 was prepared according to the following production method. With regards to the resulting cosmetic, an evaluation was made as to ultraviolet protection effect, transparency (whiteness when the cosmetic is applied) and feeling in use. The results of the evaluation are shown in Table 3.

<Method of Producing the Liquid Ultraviolet Protection Cosmetic>

Components (5) to (7) were mixed, to which were then added the powders (1) to (4) dispersed thoroughly in the component (8) by using a disperser. The components (9) and (10) were further added to the mixture and mixed uniformly, thereby producing a cosmetic.

TABLE 3

| Component (weight %) | Example | | Comparative example | | | | |
|---|---|---|---|---|---|---|---|
| | 6 | 7 | 4 | 5 | 6 | 7 | 8 |
| 1 Microparticle zinc oxide coated with silicone *1 | 7 | 3 | 10 | | | 8 | 7 |
| 2 Flake zinc oxide *2 | 1 | 1 | | 10 | | | 1 |
| 3 Complex Polymer particle including zinc oxide | 5 | 5 | | | 25 | 5 | |
| 4 Microparticle zinc oxide/titanium oxide silicone dispersion solution (28%) *3 | | 14 | | | | | |
| 5 Polyoxyethylene/methylpolysiloxanecopolymer *4 | 1 | 1 | 1 | 1 | 1 | 1 | 1 |
| 6 2-Ethylhexyl paramethoxycinnamate | 3 | 3 | 3 | 3 | 3 | 3 | 3 |
| 7 Dimethylpolysiloxane (6 cs) | 9 | 9 | 9 | 9 | 9 | 9 | 9 |
| 8 Methylcyclopolysiloxane (five-membered ring) | 30 | 30 | 30 | 30 | 30 | 30 | 30 |
| 9 Ethanol (55 v/v %) | 9.5 | 9.5 | 9.5 | 9.5 | 9.5 | 9.5 | 9.5 |
| 10 Purified water | Balance | Balance | Balance | Balance | Balance | Balance | Balance |
| Total | 100 | 100 | 100 | 100 | 100 | 100 | 100 |
| Evaluation | | | | | | | |
| UVB protective effect | ◯ | ◯ | X | X | X | Δ | Δ |
| UVA protective effect | ◯ | ◯ | X | X | Δ | X | Δ |
| Transparency | ◯ | ◯ | ◯ | Δ | Δ | ◯ | ◯ |
| Feeling in use | ◯ | ◯ | X | X | Δ | ◯ | X |

*1: Powder obtained by processing the surface of FINEX-50 (average primary particle diameter: 0.02 μm, Sakai Chemical Industry Co., Ltd.) by using silicone.
*2: Publication of JP-A8-12526, Synthetic example 2 (average size: 0.6 μm, average thickness 0.02 μm)
*3: One produced according to Example 1 in the publication of JP-A2000-290156.
*4: Silicone SH3775C (Dow Coating Toray Silicone)

Example 6 which was an embodiment of the present invention was excellent in all of the effects of protecting from ultraviolet rays of UVA and UVB, transparency and feeling in use. Example 7 which was another embodiment of the present invention and in which a part of the microparticle metal oxide was replaced by a microparticle high dispersion was also excellent in all of the effects of protection from ultraviolet rays of UVA and UVB, transparency and feeling in use.

On the other hand, Comparative Examples 4 to 8, including those containing only one of the microparticle metal oxide, the flake zinc oxide or the polymer composite particle respectively, one containing no flake zinc oxide and one containing no coated polymer composite, were poor in a UVB protective effect, transparency and feeling in use.

The invention claimed is:

1. A polymer composite particle comprising a metal oxide coated with a silicone and/or fluorine compound, wherein the metal oxide has an average particle diameter of 1 μm or less, the polymer composite particle being obtained by polymerizing a mixture comprising the coated metal oxide particle a crosslinking agent and a vinyl monomer, wherein not less than 25% by weight of said vinyl monomer based on 100% by weight of the sum total of all the monomers and the crosslinking agents has a solubility parameter of less than about 8.9.

2. The polymer composite particle of claim 1 wherein a cosmetic comprising said polymer composite particle in an amount corresponding to 5% by weight of the metal oxide and 1% by weight of 2-ethylhexyl 4-methoxycinnamate by weight of the cosmetic, results in the cosmetic having an SPF of 7 or more.

3. The polymer composite particle according to claim 1 or 2, wherein the vinyl monomer having a solubility parameter less than about 8.9 comprises an alkyl(meth)acrylate having a straight-chain or branched alkyl group which has 8 or more carbon atoms and may optionally be fluorinated.

4. The polymer composite particle according to claim 1 or 2, wherein the vinyl monomer having a solubility parameter of less than about 8.9 comprises a dimethyl polysiloxane compound having a radical polymerizable group at one terminal of a molecular chain.

5. The polymer composite particle according to claim 1 or 2, wherein the vinyl monomer having a solubility parameter less than about 8.9 comprises an alkyl(meth)acrylate having a straight-chain or branched alkyl group which has 8 or more carbon atoms and may be optionally fluorinated and a dimethyl polysiloxane compound having a radical polymerizable group at one terminal of a molecular chain.

6. The polymer composite particle according to claim 1 or 2, wherein the metal oxide is one or more types selected from the group consisting of zinc oxide, titanium oxide, cerium oxide, and mixtures thereof.

7. The polymer composite particle according to claim 1 or 2, wherein the content of the metal oxide is from 25 to 90% by weight of the polymer composite particle.

8. A method of producing the polymer composite particle as claimed in claim 1 or 2, the method comprising the steps of:

dispersing and mixing a metal oxide coated with a silicone and/or fluorine compound, a monomer component comprising a vinyl monomer having a solubility parameter less than about 8.9 and a crosslinking agent, and suspension-polymerizing the mixture.

9. A cosmetic comprising the polymer composite particle as claimed in claim 1 or 2.

10. A cosmetic composition comprising the following components (A) and (B) and the cosmetic as claimed in claim 9:

(A) a microparticle metal oxide having an average primary particle diameter of from 0.001 to 0.1 μm and (B) a flake zinc oxide having an average size of from 0.1 μm to 1 μm and an average thickness of from 0.01 μm to 0.2 μm.

11. The cosmetic composition according to claim 10, wherein the flake zinc oxide as component (B) is contained at a ratio by weight of from 0.05 to 0.4 to the total metal oxide contained in said component (A) and in said polymer composite particle.

12. Use of the polymer composite particle as claimed in claim 1 or 2 for cosmetics.

13. A cosmetic composition comprising the polymer composite particle as claimed in claim 1 or 2, further comprising other cosmetic components, and a cosmetic carrier.

14. The polymer composite particle according to claim 1, wherein the content of the crosslinking agent is from 0.1 to 75% by weight based on 100% by weight of the sum total of all the monomers and the crosslinking agents.

* * * * *